(12) United States Patent
Pan et al.

(10) Patent No.: US 12,673,130 B2
(45) Date of Patent: Jul. 7, 2026

(54) DYNAMIC ANTIMICROBIAL HYDROGEL BASED ON NATURAL RECEPTOR-LIGAND RECOGNITION, AND PREPARATION METHOD AND USE THEREOF

(71) Applicant: JIANGSU UNIVERSITY, Zhenjiang (CN)

(72) Inventors: Guoqing Pan, Zhenjiang (CN); Wenbo He, Zhenjiang (CN); Yue Ma, Zhenjiang (CN); Miao Wang, Zhenjiang (CN)

(73) Assignee: JIANGSU UNIVERSITY, Zhejiang (CN)

( * ) Notice: Subject to any disclaimer, the term of this patent is extended or adjusted under 35 U.S.C. 154(b) by 428 days.

(21) Appl. No.: 18/258,217

(22) PCT Filed: Sep. 27, 2022

(86) PCT No.: PCT/CN2022/121661
§ 371 (c)(1),
(2) Date: Jun. 19, 2023

(87) PCT Pub. No.: WO2023/216495
PCT Pub. Date: Nov. 16, 2023

(65) Prior Publication Data
US 2024/0374787 A1 Nov. 14, 2024

(30) Foreign Application Priority Data
May 12, 2022 (CN) .......................... 202210532451.4

(51) Int. Cl.
A61L 26/00 (2006.01)
(52) U.S. Cl.
CPC ......... A61L 26/008 (2013.01); A61L 26/0014 (2013.01); A61L 26/0023 (2013.01); A61L 26/0038 (2013.01); A61L 2300/252 (2013.01)

(58) Field of Classification Search
None
See application file for complete search history.

(56) References Cited

U.S. PATENT DOCUMENTS

2007/0243255 A1* 10/2007 Xu ..................... A61K 31/7034
                                                514/35
2008/0107707 A1* 5/2008 Lawson .................. A61L 27/54
                                                424/94.1
2013/0017232 A1 1/2013 Varghese et al.

FOREIGN PATENT DOCUMENTS

CN   101431983 A   5/2009
CN   110917392 A   3/2020
CN   113018417 A   6/2021

OTHER PUBLICATIONS

Mckinley C. Lawson, et al., Polymerizable Vancomycin Derivatives for Bactericidal Biomaterial Surface Modification: Structure-Function Evaluation, Biomacromolecules, 2009, pp. 2221-2234, vol. 10, No. 8.

(Continued)

*Primary Examiner* — Brian Gulledge
(74) *Attorney, Agent, or Firm* — Bayramoglu Law Offices LLC

(57) ABSTRACT

A dynamic antimicrobial hydrogel based on natural receptor-ligand recognition, and a preparation method and use thereof are provided. A ligand vancomycin and a receptor AA-based material each are first modified with a modification material, and then a photoinitiator is added to prepare a hydrogel material under irradiation of ultraviolet (UV) light. In the hydrogel, a three-dimensional (3D) network structure is formed through crosslinking. After undergoing a fracture under an external pressure, the hydrogel can rapidly heal itself through crosslinking due to a ligand-receptor interaction and a multi-hydrogen-bond interaction, which biomimics a natural ligand-receptor interaction to realize the (Continued)

Van + PEG-NHS → (DMSO, pH 8.2) → Van-M dynamics of the hydrogel material. The high antiomicrobial activity of vancomycin imparts the functionality of the hydrogel material; and the physiologically-derived monomer improves the biocompatibility and reduces the biological toxicity.

9 Claims, 6 Drawing Sheets

(56)                    References Cited

OTHER PUBLICATIONS

Mckinley C. Lawson, et al., Vancomycin Derivative Photopolymerized to Titanium Kills S. epidermidis, Clinical Orthopaedics and Related Research, 2007, pp. 96-105, No. 461.
Wenbo He, et al., Reversible dougong structured receptor-ligand recognition for building dynamic extracellular matrix mimics, PNAS, 2022, pp. 1-10, vol. 119, No. 8, e2117221119.

* cited by examiner

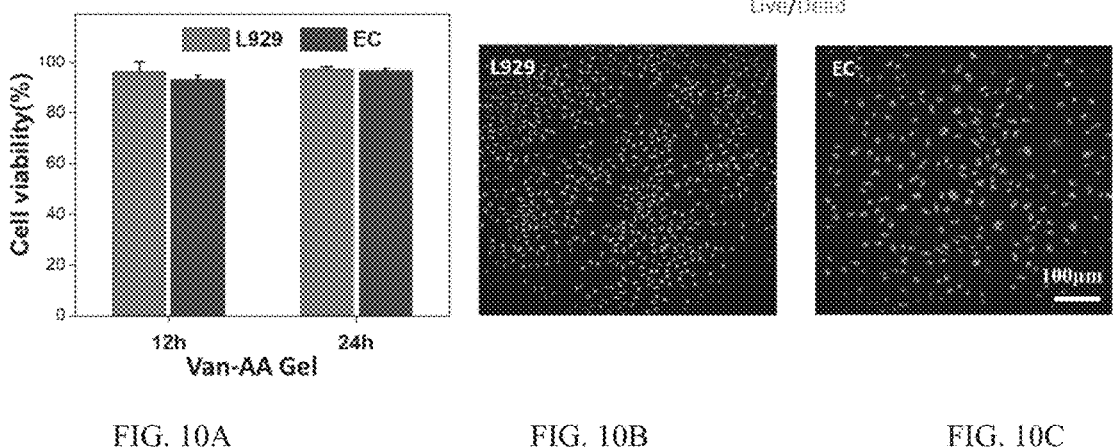
FIG. 10A                    FIG. 10B                    FIG. 10C
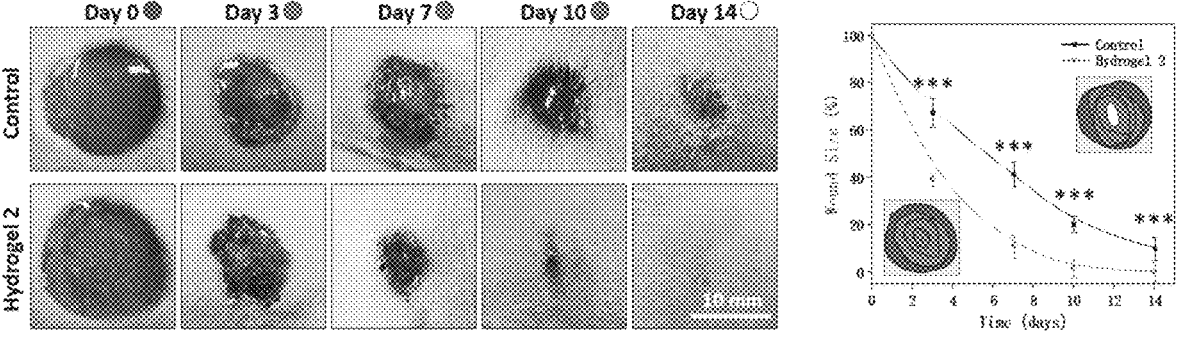
FIG. 11A                              FIG. 11B

DYNAMIC ANTIMICROBIAL HYDROGEL BASED ON NATURAL RECEPTOR-LIGAND RECOGNITION, AND PREPARATION METHOD AND USE THEREOF

CROSS REFERENCE TO THE RELATED APPLICATIONS

This application is the national phase entry of International Application No. PCT/CN2022/121661, filed on Sep. 27, 2022, which is based upon and claims priority to Chinese Patent Application No. 202210532451.4, filed on May 12, 2022, the entire contents of which are incorporated herein by reference.

TECHNICAL FIELD

The present disclosure belongs to the field of biomedical polymer materials, and specifically relates to a dynamic antimicrobial hydrogel based on natural receptor-ligand recognition, and a preparation method and use thereof.

BACKGROUND

Hydrogel materials are a group of biomedical materials with three-dimensional (3D) network structures, and are widely used in many fields such as skin repair, bone tissue repair, cell engineering, tissue engineering, drug delivery, bacterial inhibition and resistance, and emergency engineering due to their pore structures. In a clinical application, a hydrogel material is easily deformed under an action of an external force, which affects the exertion of a function of the hydrogel material.

Existing hydrogels, especially dynamic hydrogel materials (namely, injectable self-healing hydrogels), can undergo rapid automatic recovery after being deformed under an action of an external force and continue to exert their effects due to dynamic properties, which is expected to overcome insufficient mechanical properties of hydrogels, and is conducive to the promotion of hydrogels in biomedical applications. However, these hydrogels are mostly produced through chemical interactions, including: crosslinking through reversible covalent bonds and hydrogen bonds with weak bonding forces; and these hydrogels are mostly prepared from chemical substances with insufficient biocompatibility, and thus have limited biocompatibility and dynamics, making these hydrogels far from clinical applications.

A ligand-receptor interaction is based on complementarity of specific groups and adaptability with a space; and the binding through the ligand-receptor interaction leads to a decrease in free energy of a system, which is a driving force for the binding. The ligand-receptor interaction has excellent spatial complementarity and a strong chemical interaction, can allow specific binding, and exhibits an ability to achieve accurate recognition and binding. Moreover, most of the molecules that can produce this interaction are physiologically-derived substances, have excellent biocompatibility and low biological toxicity, and show promising development prospects.

SUMMARY

The present disclosure provides a dynamic antimicrobial hydrogel based on natural receptor-ligand recognition, and a preparation method and use thereof. In the present disclosure, based on natural mutual recognition between the ligand vancomycin and a dipeptide D-Ala-D-Ala (abbreviated as AA)-based receptor, ligand/receptor-based crosslinking points are formed to prepare an injectable self-healing hydrogel. The injectable self-healing hydrogel has prominent mechanical properties and excellent self-recovery and injectability, and is verified by in vitro and in vivo experiments to have excellent antimicrobial activity and clinical practical value in skin repair.

To achieve the above objective, the present disclosure provides a preparation method of a dynamic hydrogel based on natural receptor-ligand recognition, including the following steps:

(1) modification of a ligand vancomycin: dissolving vancomycin hydrochloride and a modification material in an organic solution or pure water, introducing an inert gas to remove oxygen, and adjusting a pH of a resulting solution; conducting a hydroxyl-carboxyl esterification reaction, an amino-carboxyl amidation reaction, and a transesterification reaction at a constant temperature, and after the reactions, subjecting a resulting reaction system to dialysis to obtain Van-M; and lyophilizing the Van-M, and storing a lyophilized product at −20° C. for later use;

(2) modification of a receptor AA-based material: dissolving the receptor AA-based material and a modification material in a mixed solution of an organic solution and water, introducing an inert gas to remove oxygen, and adjusting a pH of a resulting solution; conducting a hydroxyl-carboxyl esterification reaction, an amino-carboxyl amidation reaction, a transesterification reaction, and a mercapto-alkenyl addition reaction at a constant temperature, and subjecting a resulting reaction system to dialysis to obtain AA-M; and lyophilizing the AA-M, and storing a lyophilized product at −20° C. for later use; and (3) preparation of a hydrogel material: dissolving the Van-M obtained in the step (1) and the AA-M obtained in the step (2) in water, and adding a photoinitiator to trigger a crosslinking reaction under irradiation of ultraviolet (UV) light to obtain the dynamic hydrogel.

Further, in the step (1), the vancomycin hydrochloride is used in an amount of 0.2 mmol to 0.25 mmol; the modification material is acrylamide-polyethylene glycol (PEG) (3400)-N-hydroxysuccinimide or a natural bio-based polymer material, and is used in an amount of 0.15 mmol to 0.25 mmol; and an organic solvent is selected from the group consisting of tetrahydrofuran, dioxane, ethanol, dimethyl sulfoxide (DMSO), methanol, and toluene.

Further, the natural bio-based polymer material is selected from the group consisting of a (meth)acrylated or acrylamidated gelatin (Gel), sodium alginate (SA, $(C_6H_7O_6Na)_n$), chitosan (CTS, $(C_6H_{11}NO_4)_n$), polyvinyl alcohol (PA, $(C_2H_4O)_n$), cellulose $((C_6H_{10}O_5)_n)$, and hyaluronic acid (HA, $(C_{14}H_{21}NO_{11})_n$).

Further, in the step (2), the receptor AA-based material is an amino acid sequence or composite molecule including an AA short peptide at a C-terminus, and is preferably GAA or KAA.

Further, in the step (1) and the step (2), the pH is adjusted with triethylamine to 8 to 8.5; and the reactions are conducted at 25° C.

Further, the dialysis is conducted for 3 d to 7 d with a dialysis bag having a molecular weight cut-off of 1 KD to 10 KD.

Further, in the step (3), a ratio of the Van-M to the AA-M is 1:1 to 3:1, and is preferably 2:1.

Further, in the step (3), the photoinitiator is selected from the group consisting of 2-hydroxy-4'-(2-hydroxyethoxy)-2-methylpropiophenone (HHMP), 2,4-diethylthioxanthone (DETX), 4-phenylbenzophenone (PBZ), 4-methylbenzophenone (MBZ), isooctyl p-N,N-dimethylaminobenzoate (EHA), methyl o-benzoylbenzoate, ethyl p-N,N-dimethylaminobenzoate (EDB), isopropylthioxanthone (ITX), and 1-hydroxycyclohexyl phenyl ketone, and the photoinitiator has a concentration of 3 mg/mL to 5 mg/mL; the UV light has a wavelength of 365 nm; and the crosslinking reaction is conducted at 10° C. to 35° C. continuously for 10 min to 30 min.

The present disclosure also provides a dynamic hydrogel based on natural receptor-ligand recognition prepared by the preparation method described above, where in the dynamic hydrogel, vancomycin and an AA polypeptide are crosslinked based on a ligand-receptor interaction to form a 3D network structure; and after the hydrogel undergoes a fracture under an external pressure or under irradiation of UV light, the 3D network structure rapidly heals itself through crosslinking due to the ligand-receptor interaction and a multi-hydrogen-bond interaction.

The present disclosure also provides a use of the dynamic hydrogel based on natural receptor-ligand recognition in repair of an infected tissue wound.

Compared With the Prior Art, the Present Disclosure has the Following Advantages In the present disclosure, a ligand vancomycin and an AA polypeptide receptor are crosslinked through an interaction to form a 3D network structure, thereby producing a dynamic hydrogel. The interaction between the natural ligand and the receptor relies on a non-covalent interaction between the two molecules, and the chemical groups and geometries of the two molecules are perfectly complementary, such that the hydrogel can rapidly recover itself after being deformed under an external force to continue the exertion of efficacy of the hydrogel. Compared with a purely-chemical method, the bioreversible method has unique advantages in design of dynamic biomaterials. In addition, the Van-AA interaction represents the smallest and simplest receptor-ligand recognition system, and due to dynamics and biological properties, the system makes molecular modification easy and facilitates the design of a biomaterial. In the present disclosure, the natural ligand-receptor interaction and the modification of a monomer with a natural polymer improve the mechanical properties of the dynamic hydrogel material, and allow the dynamic hydrogel material to have antimicrobial activity and achieve rapid repair of a skin tissue. The hydrogel material of the present disclosure integrates dynamics, biological properties, and functionality, which is conducive to promotion of the hydrogel material in biomedical applications. Therefore, the present disclosure is expected to provide a new method for the design of a dynamic hydrogel material and the rapid repair of a skin tissue.

BRIEF DESCRIPTION OF THE DRAWINGS

FIG. 2A shows a proton nuclear magnetic resonance ($^1$H-NMR) spectrum of a vancomycin-based monomer, and FIG. 2B shows infrared (IR) spectra.

4

Figures 4A, 4B, 5:
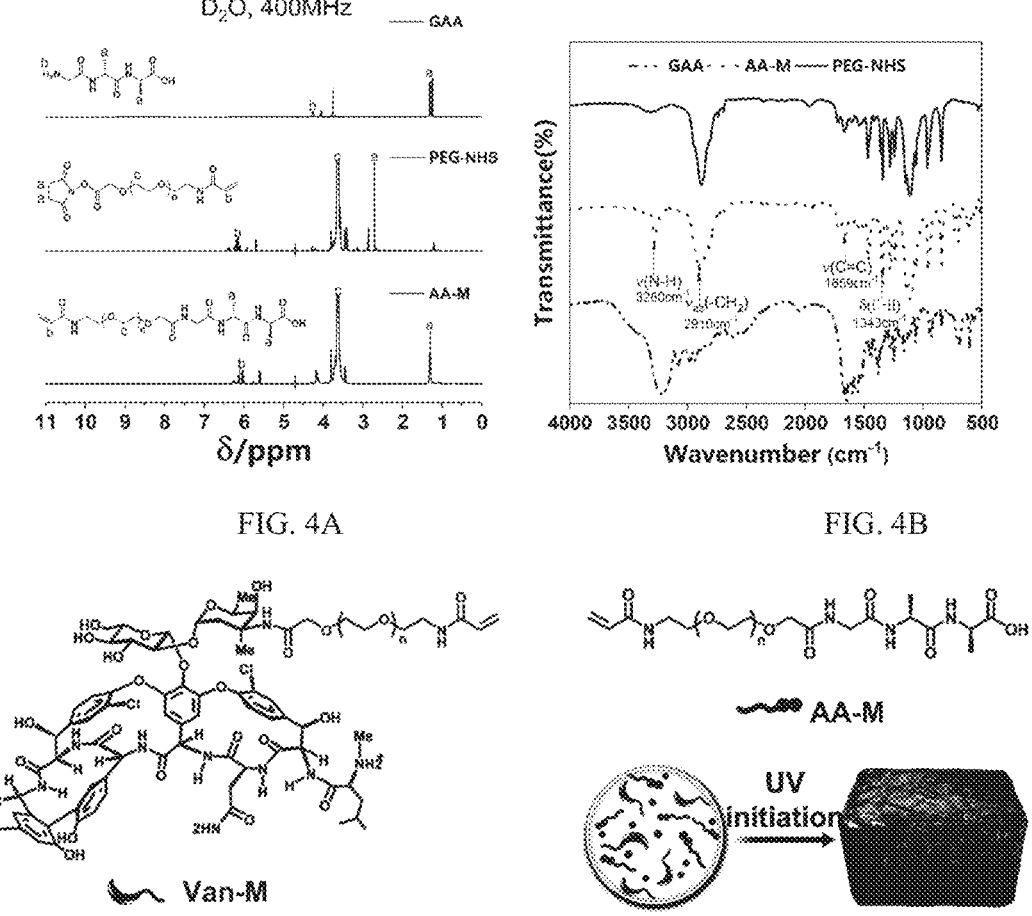
FIG. 4A shows a $^1$H-NMR spectrum of an AA-based monomer.
FIG. 4B shows IR spectra.

FIG. 5 is a schematic diagram of a preparation process of an antimicrobial hydrogel.

Figures 6A, 6B, 7A, 7B:
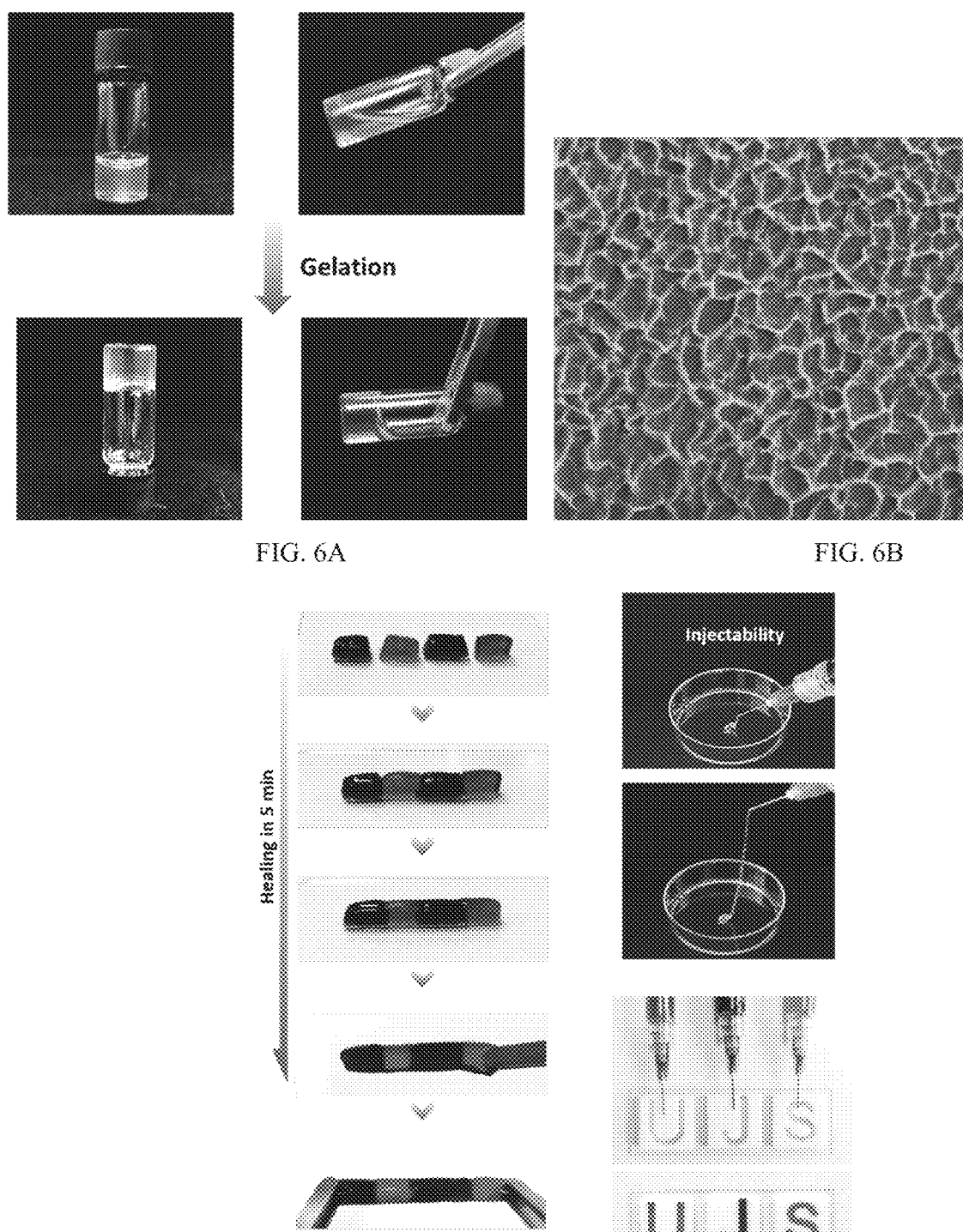

FIG. 6A shows physical pictures of the hydrogel prepared in Example 1, and FIG. 6B shows a scanning electron microscopy (SEM) image of the hydrogel.

FIG. 7A shows the self-healing performance of a hydrogel, and FIG. 7B shows the injectability of the hydrogel.

FIG. 8A, FIG. 8B, and FIG. 8C show the tensile properties and rheological patterns of a hydrogel.

Figure 9:
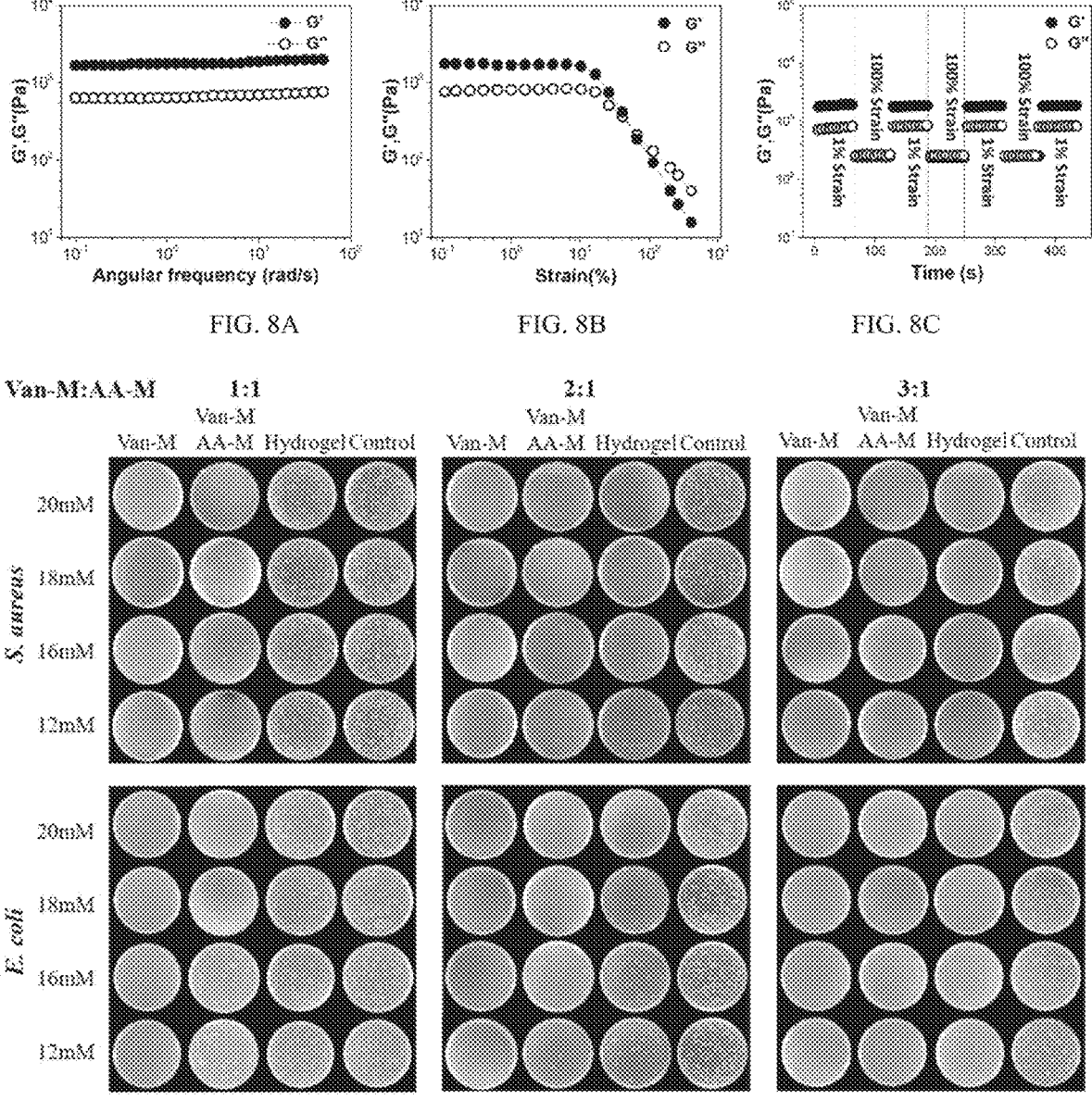

FIG. 9 shows the antimicrobial activity of a hydrogel.

FIGS. 10A-10C show the biocompatibility and cytotoxicity of a hydrogel.

FIGS. 11A-11B show an example of skin repair with a hydrogel.

Figure 12A:
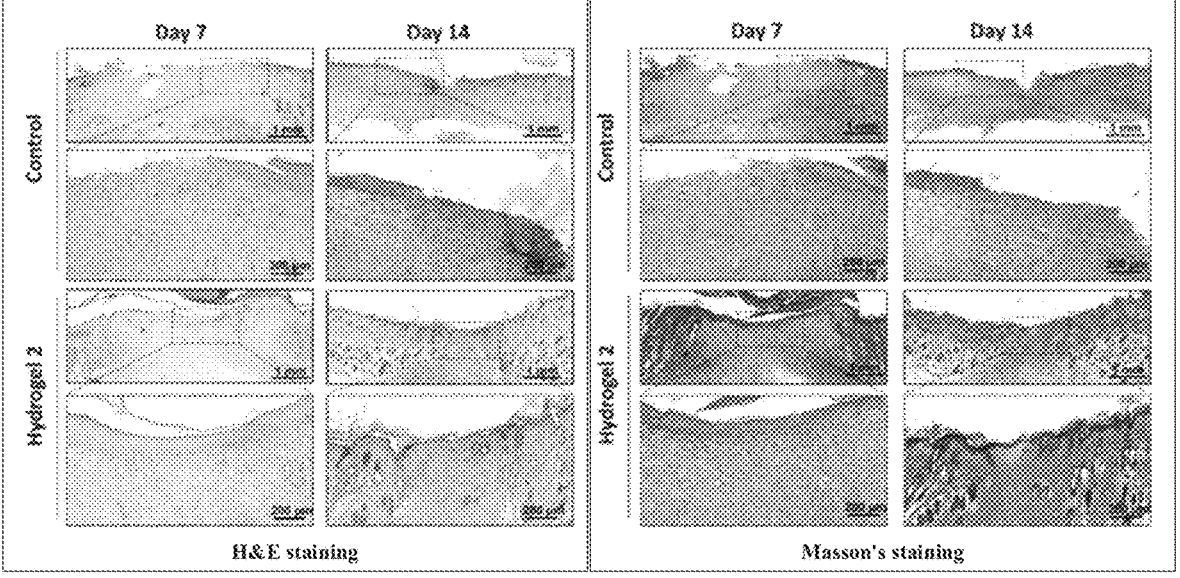
Figure 12B:
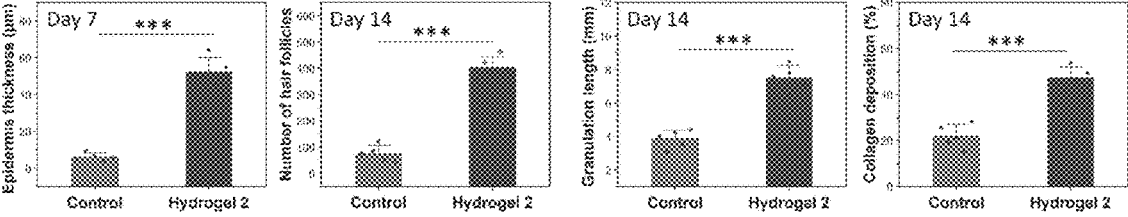

FIGS. 12A-12B show legends related to tissue sections after skin repair.

DETAILED DESCRIPTION OF THE EMBODIMENTS

In order to enable those skilled in the art to understand the present disclosure comprehensively, the present disclosure will be further described below in conjunction with the accompanying drawings and specific examples, but the protection scope of the present disclosure is not limited thereto.

Example 1

Figure 1:
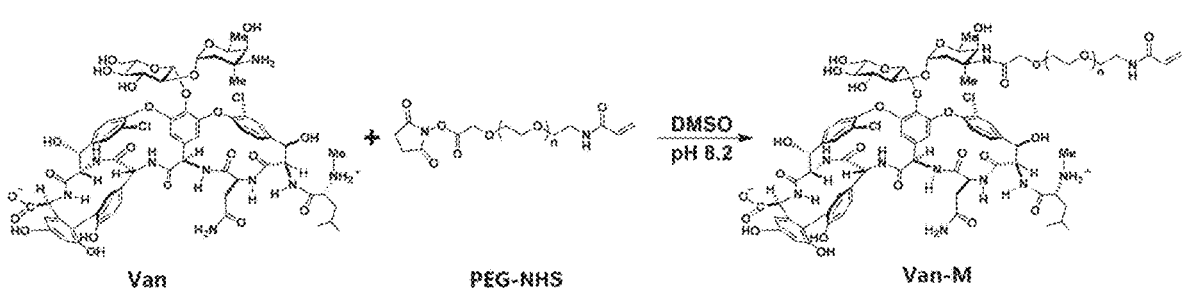
FIG. 1 is a schematic diagram of preparation of a vancomycin-based monomer as a ligand.

(1) Modification of a Ligand Vancomycin 0.33 g (0.22 mmol) of vancomycin hydrochloride and 0.72 g (0.2 mmol) of acrylamide-PEG (3400)-N-hydroxysuccinimide were dissolved in 5 mL of DMSO, $Ar_2$ was then introduced for 15 min to remove oxygen, the resulting solution was rapidly mixed, and a pH of the solution was adjusted with triethylamine to 8.2; the solution was transferred to a heated thermostatic mixer and subjected to a reaction at 25° C. for 24 h, where a process of the reaction is shown in FIG. 1; and the resulting reaction system was subjected to dialysis with a 2 kDa dialysis bag for 5 d to obtain a product vancomycin-PEG-acrylamide (Van-M), and the Van-M was lyophilized for 2 d and then stored in a sample bottle at –20° C.

The prepared Van-M was dissolved in $D_2O$, and a 1H-NMR spectrum of the Van-M was acquired by nuclear magnetic resonance spectroscopy (NMRS) (Bruker, Germany, 400 MHZ). Test results are shown in FIG. 2A. A fourier transform infrared (FT-IR) spectrum of the prepared Van-M was acquired by a Nicolet IS50 FT-IR spectrometer (Thermo Fisher, USA) with a wavenumber range of 4,000 $cm^{-1}$ to 400 $cm^{-1}$ and a resolution of 4 $cm^{-1}$, and test results are shown in of FIG. 2B. The results show that the acrylamide-PEG group was successfully grafted onto the ligand vancomycin molecule.

Figure 3:
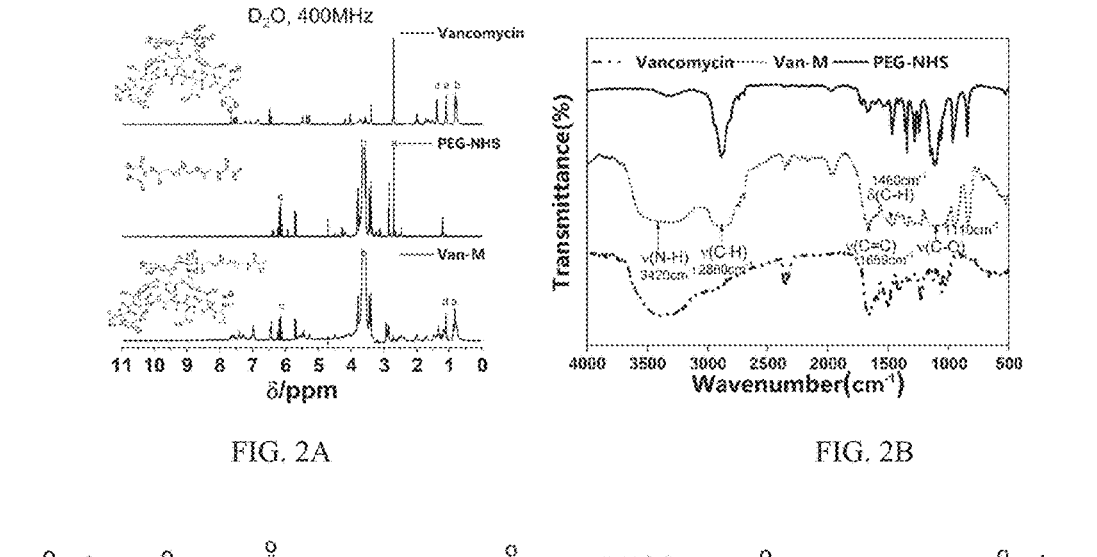
FIG. 3 is a schematic diagram of preparation of an AA-based monomer.

(2) Modification of a Receptor AA-Based Material 48 mg (0.22 mmol) of GAA and 0.72 g (0.2 mmol) of acrylamide-PEG (3400)-N-hydroxysuccinimide were dissolved in a mixture of 4 mL of DMSO and ultrapure water (UPW) (v/v=1:1); $Ar_2$ was then introduced for 15 min to remove oxygen, the resulting solution was rapidly mixed, and a pH of the solution was adjusted with triethylamine to 8.2; the solution was transferred to a heated thermostatic mixer (SD1-1000, Titan Tech, CN), and subjected to a reaction at 25° C. for 24 h, where an equation of the reaction is shown in FIG. 3; and the resulting reaction system was subjected to dialysis with a 2 kDa dialysis bag for 5 d to obtain a product GAA-PEG-acrylamide (AA-M), and the AA-M was lyophilized (SCIENTZ-10N, SCIENTZ Bio Tech, CN) for 2 d, and then stored in a sample bottle at −20° C.

In the present disclosure, all receptor-based monomers were prepared by this method.

The prepared AA-M was dissolved in $D_2O$, and a $^1$H-NMR spectrum of the AA-M was acquired by NMRS (Bruker, Germany, 400 MHZ). Test results are shown in FIG. 4A. An FT-IR spectrum of the prepared AA-M was acquired by a Nicolet IS50 FT-IR spectrometer (Thermo Fisher, USA) with a wavenumber range of 4,000 cm$^{-1}$ to 400 cm$^{-1}$ and a resolution of 4 cm-1, and test results are shown in FIG. 4B. The results show that the acrylamide-PEG group was successfully grafted onto the receptor AA molecule.

(3) Preparation of a Hydrogel Material

10 μmol of Van-M and 5 μmol of AA-M were dissolved in 450 μL of UPW and then rapidly stirred to obtain a homogeneous solution; and then 50 μL of a 5 mg/mL HHMP photoinitiator solution was added to the homogeneous solution, and a reaction was initiated under irradiation of 365 nm UV light, and performed at 25° C. for 30 min, to obtain a target product Hydrogel 1. A process of the reaction is shown in FIG. 5. The physical pictures and SEM image of the hydrogel are shown in FIGS. 6A-6B. It can be seen from FIGS. 6A-6B that a hydrogel material with a crosslinked network structure was successfully prepared.

Example 2

(1) Modification of a Ligand Vancomycin

It was the same as in Example 1.

(2) Modification of a Receptor AA-Based Material

It was the same as in Example 1.

(3) Preparation of a Hydrogel Material

15 μmol of Van-M and 5 μmol of AA-M were dissolved in 450 μL of UPW and then rapidly stirred to obtain a homogeneous solution; and then 50 μL of a 5 mg/mL HHMP photoinitiator solution was added to the homogeneous solution, and a reaction was initiated under irradiation of 365 nm UV light, and performed at 25° C. for 30 min, to obtain a target product Hydrogel 2.

Example 3

(1) Modification of a Ligand Vancomycin

It was the same as in Example 1.

(2) Modification of a Receptor AA-Based Material

It was the same as in Example 1.

(3) Preparation of a Hydrogel Material

5 μmol of Van-M and 5 μmol of AA-M were dissolved in 450 μL of UPW and then rapidly stirred to obtain a homogeneous solution; and then 50 μL of a 5 mg/mL HHMP photoinitiator solution was added to the homogeneous solution, and a reaction was initiated under irradiation of 365 nm UV light, and performed at 25° C. for 30 min, to obtain a target product Hydrogel 3.

In Examples 1 to 3, the modification materials for the ligand vancomycin and the receptor AA-based material both are acrylamide-PEG (3400)-N-hydroxysuccinimide, but a natural bio-based polymer material can also be used; and the natural bio-based polymer material is selected from the group consisting of (meth)acrylated or acrylamidated Gel, SA $((C_6H_7O_6Na)_n)$, CTS $((C_6H_{11}NO_4)_n)$, PA $((C_2H_4O)_n)$, cellulose $((C_6H_{10}O_5)_n)$, and HA $((C_{14}H_{21}NO_{11})_n)$. The receptor AA-based material is an amino acid sequence or composite molecule including an AA short peptide at a C-terminus, and is preferably GAA or KAA. The organic solvent can also be selected from the group consisting of dioxane, ethanol, DMSO, methanol, and toluene. The photoinitiator can also be selected from the group consisting of DETX, PBZ, MBZ, EHA, methyl o-benzoylbenzoate, EDB, ITX, and 1-hydroxycyclohexyl phenyl ketone, and the photoinitiator has a concentration of 3 mg/mL to 5 mg/mL; the UV light has a wavelength of 365 nm; and the crosslinking reaction is conducted at 10° C. to 35° C. continuously for 10 min to 30 min.

In the hydrogel prepared by the present disclosure, vancomycin and an AA polypeptide are crosslinked based on a ligand-receptor interaction to form a 3D network structure; and after the hydrogel undergoes a fracture under an external pressure or under irradiation of UV light, the 3D network structure is able to rapidly heal itself through crosslinking due to the ligand-receptor interaction and a multi-hydrogen-bond interaction.

Dynamic Properties of the Hydrogel

The self-healing performance of the hydrogel of the present disclosure was further investigated by the following two methods:

1. Four hydrogel samples stained with methylene blue and methyl orange were placed on glass slides, respectively, the glass slides were arranged in a crossing manner according to colors, and a self-healing process of the hydrogel was photographed by a camera. After the hydrogel was completely healed, a healed hydrogel was immediately stretched to observe a mechanical strength of the healed hydrogel.

2. A thin hydrogel layer (1 mm) was cut with a scalpel to form an incision, and then a healing process was recorded at a predetermined interval under a microscope equipped with a digital camera.

The injectability was tested as follows: 500 μL of the hydrogel was placed in a syringe, and then the hydrogel was injected through a 22 G needle and photographed by a camera. Three hydrogel samples stained with methylene blue, methyl orange, and crystal violet were respectively placed in three syringes, and then injected into U, J, and S molds through 22 G needles; and the molds were taken out, and the injected hydrogels were photographed, as shown in FIG. 7B.

A self-healing process of the hydrogel is shown in FIG. 7A, and experimental results show that the prepared hydrogel exhibited excellent self-recovery and injectability.

Mechanical Properties of the Hydrogel

The mechanical properties of the hydrogel play a crucial role in clinical applications of the hydrogel. The hydrogel of the present disclosure was subjected to a rheological measurement by a rheometer (Anton Paar, MCR302). The hydrogel was subjected to the following rheological tests: (1) The hydrogel was subjected to frequency scanning at a strain of 5% to explore changes in a storage modulus (G') and a loss modulus (G) of the hydrogel, and test results are shown in FIG. 8A. (2) A dynamic strain range at ω=10 rad/s was 0.01% to 1,000%. The changes of a storage modulus (G') and a loss modulus (G") of the hydrogel in a strain interval of 1% to 100% (the low strain 1% lasted for 1 min and the high strain 100% lasted for 1 min) were measured to determine the changes of the storage modulus (G') and the loss modulus (G") of the hydrogel in a critical strain range and a linear vicoelasticity range, and test results are shown in FIG. 8B. It can be known from the data in the figure that the hydrogel in the present disclosure has an excellent mechanical strain (as shown in FIG. 8C) and exhibits the characteristics of a dynamic hydrogel.

An Example of Antimicrobial Activity of the Hydrogel

A colony-forming unit (CFU) method was used to test the antimicrobial activities of the hydrogel to *Staphylococcus aureus* (*S. aureus*, Gram-positive bacteria) and *Escherichia coli* (*E. coli*, gram-negative bacteria), and qualitative and quantitative analysis was conducted. In order to determine the antimicrobial activities of the hydrogel, a Van-M monomer group (a), a Van-M/AA-M mixed solution group (b), and a blank group (d) were adopted as control groups and a hydrogel group was adopted as an experimental group to conduct synchronous experiments. Specific operations were as follows: Bacteria were cultivated overnight in a Luria-Bertani (LB) broth at 37° C.; an optical density at 600 nm was adjusted to 0.1, namely, about $10^8$ CFU/mL; a bacterial solution serially diluted ($10^4$ CFU/mL) was divided into four groups (a, b, c, and d) each of 1 mL, where Van-M was added to a, Van-M and AA-M were added to b, 100 mg of the Van-AA hydrogel was added to c, and d was adopted as a blank group; and the resulting mixtures each were incubated at 37° C. for 24 h, then coated on an LB solid medium, and further incubated at 37° C. for 20 h, and then a number of colonies on an agar plate was counted. A Van-M concentration in the Van-AA hydrogel was taken as a benchmark. A result was expressed by a bacterial survival rate, and 3 replicates were set for each group. Experimental results are shown in FIG. 9. The results show that the hydrogel exhibited an excellent antimicrobial activity to both *E. coli* and *S. aureus*.

Cytotoxicity and Compatibility Experiments of the Hydrogel

The cytotoxicity of the hydrogel was evaluated by cultivating cells with a leaching liquor of the hydrogel. 500 μL of the hydrogel was added to a cell chamber placed in a 24-well plate, then 1 mL of a medium was added to the plate, and the plate was incubated for 24 h to obtain a hydrogel extract; cells normally cultivated ($5 \times 10^4$ cells/well, 100 μL) were inoculated into a 96-well plate and incubated for 6 h, then a medium was removed, and the leaching liquor of the hydrogel Van-AA was added; the cells were incubated at 37° C. and 5% $CO_2$ for 12 h and 24 h, 10 μL of a CCK-8 solution was added to each well of the 96-well plate, and the cells were incubated at 37° C. for 3 h; and the absorbance at 450 nm was determined with a microplate spectrophotometer. Six parallel replicates were set for each sample.

Live/dead cell staining was also used to demonstrate the low cytotoxicity on a biological surface. The cells incubated with the hydrogel extract ($5 \times 10^4$ cells/well, 1 mL) were washed with PBS 3 times, 200 μL of a calcein/PI staining working solution was added to each well, and the cells were incubated for 15 min, then washed with PBS 3 times, and observed under a fluorescence microscope. The Image-Pro Plus software was used to process a fluorescence image. Experimental results are shown in FIGS. 10A-10C. The cell lines used in this experiment were L929 and HUVEC.

The results show that the hydrogel material of the present disclosure had a negligible effect on the reproduction of cells, was basically non-toxic, and could be considered for clinical applications.

An Example of Use of the Hydrogel in Skin Repair 25 healthy SD rats were taken and cut at their backs to form a 1.5 cm wound, and 200 μL of $10^8$ CFU/mL *S. aureus* was injected subcutaneously. The rats were divided into 5 groups with 5 rats in each group. A group was a control group; and the other groups were treated with a Tegaderm dressing, Hydrogel 1 (Van-M: AA-M=1:1), Hydrogel 2 (Van-M: AA-M=2:1), and Hydrogel 3 (Van-M: AA-M=3:1), respectively. The wound was photographed and recorded at day 0, day 3, day 7, day 10, and day 14; and a wound healing time was recorded, and a wound healing rate was calculated. To explore the wound healing conditions, a wound was subjected to H&E and Masson's staining on day 7 and day 14. An epidermal thickness, a number of hair follicles, a width of a skin granular layer, and a thickness of collagen deposition were counted. Results are shown in FIGS. 11A-11B. The results show that the antimicrobial hydrogel material of the present disclosure exhibited a bactericidal effect on bacteria in rats, could accelerate the wound healing, and caused no damage to parts other than an injured part. FIGS. 12A-12B show legends related to tissue sections after skin repair, and it can be seen from FIGS. 12A-12B that the hydrogel can promote the repair of an injured tissue and the regeneration of a new tissue without affecting surrounding tissues.

The above examples are preferred implementations of the present disclosure, but the present disclosure is not limited to the above implementations. Any obvious improvement, substitution, or modification made by those skilled in the art without departing from the essence of the present disclosure should fall within the protection scope of the present disclosure.

What is claimed is:

1. A preparation method of a dynamic hydrogel based on a natural receptor-ligand recognition, comprising the following steps:

(1) modification of a ligand vancomycin by dissolving vancomycin hydrochloride and a modification material in an organic solution or pure water to obtain a first resulting solution, introducing an inert gas in the first resulting solution to remove oxygen, and adjusting a pH of the first resulting solution to obtain a second resulting solution; conducting a hydroxyl-carboxyl esterification reaction, an amino-carboxyl amidation reaction, and a transesterification reaction on the second resulting solution at a constant temperature to obtain a first resulting reaction system, and after the hydroxyl-carboxyl esterification reaction, the amino-carboxyl amidation reaction, and the transesterification reaction, subjecting the first resulting reaction system to a dialysis to obtain Van-M; and lyophilizing the Van-M to obtain a first lyophilized product, and storing the first lyophilized product at −20° C. for later use;

(2) modification of a receptor AA-based (dipeptide D-Ala-D-Ala based) material by dissolving the receptor AA-based material and the modification material in a mixed solution of the organic solution and water to obtain a third resulting solution, introducing the inert gas in the third resulting solution to remove oxygen, and adjusting a pH of the third resulting solution to obtain a fourth resulting solution; conducting the hydroxyl-carboxyl esterification reaction, the amino-carboxyl amidation reaction, the transesterification reaction, and a mercapto-alkenyl addition reaction on the fourth resulting solution at the constant temperature to obtain a second resulting reaction system, and subjecting the second resulting reaction system to the dialysis to obtain AA-M; and lyophilizing the AA-M to obtain a second lyophilized product, and storing the second lyophilized product at −20° C. for later use; and (3) preparation of a hydrogel material by dissolving the Van-M obtained in the step (1) and the AA-M obtained in the step (2) in the water to obtain a fifth resulting solution, and adding a photoinitiator in the fifth resulting solution to trigger a crosslinking reaction under irradiation of ultraviolet light to obtain the dynamic hydrogel.

2. The preparation method of the dynamic hydrogel based on the natural receptor-ligand recognition according to claim 1, wherein in step (1), the vancomycin hydrochloride is used in an amount of 0.2 mmol to 0.25 mmol; the modification material is acrylamide-polyethylene glycol (3400)-N-hydroxysuccinimide or a natural bio-based polymer material and is used in an amount of 0.15 mmol to 0.25 mmol; and the organic solution is selected from the group consisting of tetrahydrofuran, dioxane, ethanol, dimethyl sulfoxide, methanol, and toluene.

3. The preparation method of the dynamic hydrogel based on the natural receptor-ligand recognition according to claim 2, wherein the natural bio-based polymer material is selected from the group consisting of a (meth)acrylated or acrylamidated gelatin (Gel), sodium alginate (SA, $(C_6H_7O_6Na)_n$), chitosan (CTS, $(C_6H_{11}NO_4)_n$, polyvinyl alcohol (PA, $(C_2H_4O)_n$), cellulose $((C_6H_{10}O_5)_n)$, and hyaluronic acid (HA, $(C_{14}H_{21}NO_{11})_n$).

4. The preparation method of the dynamic hydrogel based on the natural receptor-ligand recognition according to claim 1, wherein in step (2), the receptor AA-based material is an amino acid sequence or a composite molecule comprising an AA short peptide at a C-terminus, wherein the AA short peptide is GAA or KAA.

5. The preparation method of the dynamic hydrogel based on the natural receptor-ligand recognition according to claim 1, wherein in step (1) and step (2), the pH is adjusted with triethylamine to 8 to 8.5; and the constant temperature is 25° C.

6. The preparation method of the dynamic hydrogel based on the natural receptor-ligand recognition according to claim 1, wherein the dialysis is conducted for 3 d to 7 d with a dialysis bag having a molecular weight cut-off of 1 KD to 10 KD.

7. The preparation method of the dynamic hydrogel based on the natural receptor-ligand recognition according to claim 1, wherein in step (3), a ratio of the Van-M to the AA-M is 1:1 to 3:1.

8. The preparation method of the dynamic hydrogel based on the natural receptor-ligand recognition according to claim 1, wherein in step (3), the photoinitiator is selected from the group consisting of 2-hydroxy-4'-(2-hydroxyethoxy)-2-methylpropiophenone (HHMP), 2,4-diethylthioxanthone (DETX), 4-phenylbenzophenone (PBZ), 4-methylbenzophenone (MBZ), isooctyl p-N,N-dimethylaminobenzoate (EHA), methyl o-benzoylbenzoate, ethyl p-N,N-dimethylaminobenzoate (EDB), isopropylthioxanthone (ITX), and 1-hydroxycyclohexyl phenyl ketone, and the photoinitiator has a concentration of 3 mg/mL to 5 mg/mL; the ultraviolet light has a wavelength of 365 nm; and the crosslinking reaction is conducted at 10° C. to 35° C. continuously for 10 min to 30 min.

9. The preparation method of the dynamic hydrogel based on the natural receptor-ligand recognition according to claim 7, wherein in step (3), the ratio of the Van-M to the AA-M is 2:1.

* * * * *